US011395864B2

(12) United States Patent
Fallis et al.

(10) Patent No.: US 11,395,864 B2
(45) Date of Patent: Jul. 26, 2022

(54) SETTABLE BONE VOID FILLER

(71) Applicant: DSM IP Assets, B.V., Heerlen (NL)

(72) Inventors: Andrew Fallis, Springfield, PA (US); Steven Leonhardt, Spring City, PA (US); Justin Kontra, Downingtown, PA (US); Rakesh Batish, Phoenixville, PA (US); Timothy Ringeisen, Exton, PA (US)

(73) Assignee: DSM IP ASSETS B.V., Heerlen (NL)

( * ) Notice: Subject to any disclaimer, the term of this patent is extended or adjusted under 35 U.S.C. 154(b) by 292 days.

(21) Appl. No.: 16/305,117

(22) PCT Filed: Jun. 12, 2017

(86) PCT No.: PCT/US2017/037064
§ 371 (c)(1),
(2) Date: Nov. 28, 2018

(87) PCT Pub. No.: WO2017/214635
PCT Pub. Date: Dec. 14, 2017

(65) Prior Publication Data
US 2020/0324026 A1 Oct. 15, 2020

Related U.S. Application Data

(60) Provisional application No. 62/348,575, filed on Jun. 10, 2016.

(51) Int. Cl.
*A61L 27/46* (2006.01)
*A61L 27/52* (2006.01)
*A61L 27/58* (2006.01)
*A61K 33/42* (2006.01)
*A61K 35/32* (2015.01)

(52) U.S. Cl.
CPC .............. *A61L 27/46* (2013.01); *A61L 27/52* (2013.01); *A61L 27/58* (2013.01); *A61L 2400/06* (2013.01); *A61L 2430/02* (2013.01); *A61L 2430/12* (2013.01)

(58) Field of Classification Search
CPC .......... A61L 27/46; A61L 27/52; A61L 27/58; A61L 2400/06; A61L 2430/02; A61L 2430/12
See application file for complete search history.

(56) References Cited

U.S. PATENT DOCUMENTS

| | | | |
|---|---|---|---|
| 4,171,544 A | 10/1979 | Hench et al. | |
| 4,518,430 A | 5/1985 | Brown et al. | |
| 5,053,212 A | 10/1991 | Constantz et al. | |
| 5,129,905 A | 7/1992 | Constantz | |
| 5,284,655 A * | 2/1994 | Bogdansky | |
| 5,496,399 A | 3/1996 | Ison et al. | |
| 5,571,493 A | 11/1996 | Fulmer et al. | |
| 5,782,971 A | 7/1998 | Constantz et al. | |
| 5,866,155 A | 2/1999 | Laurencin et al. | |
| 5,972,384 A | 10/1999 | Thut et al. | |
| 6,929,692 B2 | 8/2005 | Tas | |
| 7,156,880 B2 | 1/2007 | Evans et al. | |
| 7,166,133 B2 | 1/2007 | Evans et al. | |
| 7,235,107 B2 | 6/2007 | Evans et al. | |
| 7,241,316 B2 | 7/2007 | Evans et al. | |
| 7,723,395 B2 | 5/2010 | Ringeisen et al. | |
| 7,833,278 B2 | 11/2010 | Evans et al. | |
| 7,887,598 B2 | 2/2011 | Evans et al. | |
| 7,892,291 B2 | 2/2011 | Evans et al. | |
| 8,133,500 B2 | 3/2012 | Ringeisen et al. | |
| 8,163,032 B2 | 4/2012 | Evans et al. | |
| 8,389,588 B2 | 3/2013 | Ringeisen et al. | |
| 8,419,802 B2 | 4/2013 | Evans et al. | |
| 8,425,619 B2 | 4/2013 | Evans et al. | |
| 8,435,306 B2 | 5/2013 | Evans et al. | |
| 8,445,554 B2 | 5/2013 | Ringeisen et al. | |
| 8,623,094 B2 | 1/2014 | Evans et al. | |
| 9,283,074 B2 | 3/2016 | Evans et al. | |
| 9,308,076 B2 | 4/2016 | Ringeisen et al. | |
| 9,981,061 B2 | 5/2018 | Evans et al. | |
| 2003/0055512 A1 | 3/2003 | Genin et al. | |
| 2004/0137032 A1 | 7/2004 | Wang | |
| 2005/0208094 A1* | 9/2005 | Armitage | |
| 2006/0233851 A1 | 10/2006 | Simon et al. | |
| 2007/0098799 A1 | 5/2007 | Zhang et al. | |
| 2008/0063681 A1* | 3/2008 | Simon | |
| 2010/0112032 A1* | 5/2010 | Geulcher | |
| 2012/0121660 A1 | 5/2012 | Akella et al. | |
| 2012/0276164 A1* | 11/2012 | Tuominen | |
| 2013/0244856 A1 | 9/2013 | Nash et al. | |

FOREIGN PATENT DOCUMENTS

WO 2003024316 3/2003

OTHER PUBLICATIONS

International Search Report dated Aug. 4, 2017.
Written Opinion dated Aug. 4, 2017.

* cited by examiner

*Primary Examiner* — Alma Pipic
(74) *Attorney, Agent, or Firm* — Kevin M. Bull

(57) ABSTRACT

The invention provides composite materials that form a biocompatible and bioresorbable settable ceramic-forming composition, and that possesses high strength when set and other desirable mechanical properties. The composite materials may include additive materials that provide beneficial advantages in the handling and physical properties of the material. When a hydrated precursor, the composite material is capable of being injected through cannulas for placement in treatment sites. The composite material provided desirable handling properties and sets in a clinically relevant time period.

19 Claims, 5 Drawing Sheets

| | |
|---|---|
| 0. No material left on glove. Product covers <10% of glove. No visible size reduction of sample from beginning of rolling to end. Passing | |
| 1. Almost no product left on glove. Product covers <25% of area of glove product encountered. No visible size reduction of sample from beginning of rolling to end. Passing | |
| 2. Almost no to little product is left on glove. Product covers <50% of area of glove product encountered. No visible size reduction of sample from beginning of rolling to end. Passing | |
| 3. Thin amount of product left over a significant area of the glove. Product covers > 50% of area of glove product encountered. No to small visible size reduction of sample form beginning of rolling to end. Passing | |
| 4. Medium to large masses of product left on glove. Significant reduction in size of sample from beginning of rolling to end. Covers more than 60% of area of glove product encountered. Failed | |
| 5. Large masses of product left on glove. Significant reduction in size of sample from beginning of rolling to end. Covers more than 70% of area of glove product encountered. Failed | |

Fig. 2

SETTABLE BONE VOID FILLER

CROSS REFERENCE TO RELATED APPLICATIONS

This application is the US National Phase application of International Application No. PCT/US2017/037064, filed 12 Jun. 2017, which designated the US and claims priority to U.S. Provisional Patent Application No. 62/348,575, filed 10 Jun. 2016, the entire contents of each of which are hereby incorporated by reference.

FIELD OF THE INVENTION

This invention relates to composite materials containing apatite forming calcium phosphate reactants useful as human or animal implantable bioceramics and for other purposes. The invention further relates to injectable, or formable, biocompatible composite materials that can be used for reinforcement in bone fractures, dental implants, bone implants or prostheses and the like.

BACKGROUND OF THE INVENTION

Calcium phosphates are the principal constituent of hard tissues (bone, cartilage, tooth enamel and dentine). Naturally-occurring bone mineral is made of nanometer-sized, poorly-crystalline calcium phosphate with an apatitic structure. The apatitic calcium phosphate of bone is distinguishable from the more crystalline hydroxyapatites and non-stoichiometric hydroxyapatites by its distinctive x-ray diffraction pattern. Unlike the ideal stoichiometric crystalline hydroxyapatite, $Ca_{10}(PO_4)_6(OH)_2$, with atomic Ca/P ratio of 1.67, the composition of bone mineral is significantly different and may be represented by the following formula $Ca_{8.3} (PO_4)_{4.3} (HPO4, CO_3)_{1.7} (OH, CO_3)_{0.3}$.

Bone mineral non-stoichiometry is primarily due to the presence of divalent ions, such as $CO_3^{2-}$ and $HPO_4^{2-}$, which are substituted for the trivalent $PO_4^{3-}$ ions. Substitution by $HPO_4^{2-}$ and $CO_3^{2-}$ ions produces a change of the Ca/P ratio, resulting in Ca/P ratio which may vary between 1.50 to 1.70, depending on the age and bony site. Generally, the Ca/P ratio increases during aging of bone, suggesting that the amount of carbonate species typically increases for older bones. It is the Ca/P ratio in conjunction with nanocrystalline size and the poorly-crystalline nature that yields specific solubility property of the bone minerals. Bone tissues undergo constant tissue repair regulated by the mineral-resorbing cells (osteoclasts) and mineral-producing cells (osteoblasts), therefore the solubility behavior of minerals is important in maintaining a delicate metabolic balance between these cell activities.

Synthetic bone graft material made to closely resemble natural bone minerals can be a useful replacement for natural bone. Acceptable synthetic bone can avoid the problem of availability and harvesting of autologous bone (patient's own bone) and the risks and complications associated with allograft bone (bone from a cadaver), such as risks of viral transmission. An ideal synthetic bone graft should possess at least the following properties: (1) it should be chemically biocompatible; (2) it should provide some degree of structural integrity in order to keep the graft in place and intact until the patient's own bone heals around it; (3) it should be resorbable so that the patient's own bone ultimately replaces the graft. Additionally, for some applications where it may be necessary to incorporate cells and/or biomolecules into the synthetic bone material, it may be beneficial that the process used to form the material employ low temperatures and chemically mild conditions. Similar criteria are also important for other hard tissue grafts (e.g. cartilage).

Calcium phosphates have been used in biomedical devices because they provide many advantages over alternative conventional materials. For instance, it eliminates the need for post-therapy surgery to remove the device and degrades in the human body to biocompatible, bioresorbable products.

Even when the properties of biocompatibility and bioresorbability have been met, the calcium phosphate used in the biomedical device may not have the appropriate range of mechanical properties required in a particular application. Biocompatible ceramics have been reported to have excellent compatibility with bone, but the material may lack the necessary strength, flexibility or other mechanical property. Thus, ceramic materials alone, whether superbly biocompatible or not, may not meet all the requirements of an in vivo medical device.

Previously described settable calcium phosphate bone fillers and cements have disadvantages related to their handling and injectability properties. In order to be utilized as an injectable material, the previously described settable ceramic products must make accommodations to the formulation to allow for injection through a narrow gauge needle as may be utilized in orthopedic and dental applications. One accommodation often made to allow for injection is to increase the liquid content in the cement composition, such that these materials are overly hydrated, resulting in a thin, liquid-like initial material that can readily be injected. However, the runnier material is difficult to place in the surgical site, tends to migrate easily away from the site, and also suffers from compromised strength in final set form. An alternative accommodation is to utilize cement formulations that are designed to set very slowly, providing a lengthened working time for the material and thereby avoiding premature set of the material within the delivery system. However, this increase in working time of the cement also results in prolonged surgical procedure times, as the surgeon must additionally wait for the cementitious material to harden sufficiently before surgical hardware such as screws and plates can be placed, and before closing the surgical site, to ensure the cement material is set enough to avoid unwanted migration. A cement composition desirably possesses handling properties that allow the surgeon to manipulate the product without the material being degraded, such as by excessive adherence to unwanted surfaces (e.g., gloves) or having a crumbly texture that results in dissociation of the material as it is manipulated by the surgeon.

It is known that composite materials may possess a blend of the attributes and properties of the component materials comprising the composite. Therefore, it is desirable to provide composite material as a bioresorbable bone substitute which advantageously possesses superior bioresorbability, biocompatibility and bone reossification capability. It is further desirable to provide a composite material suitable as a bone substitute which possesses desirable physical characteristics, namely ease of handling, and a suitable working time for medical applications, such that the composite material retains the capability of readily being injected or placed, at least for a desired period of time after hydration, whether through a narrow gauge needle as may be used in orthopedic and dental procedures, or kneaded or formed by hand and placed at the desired site, while still retaining clinically relevant set times (e.g., less than 10 minutes), such that the composition may be useful in medical and dental applications.

SUMMARY OF THE INVENTION

Described herein is a composite material that is a biocompatible and bioresorbable settable ceramic-forming composition, and that possesses high strength when set and other desirable mechanical properties. The composite material may provide a desirable set-time for the hydrated precursor cement slurry of less than 10 minutes, may remain readily injectable through a narrow gauge cannula by forces readily achievable by hand, and may possess desirable handling characteristics as a hydrated precursor, such that it may be easily worked or maneuvered without excessively sticking to unwanted surfaces or dissociation by forming crumbs or falling apart, due to the materials cohesiveness. The composite material may avoid tissue damage that may be found with excessively exothermic reactions, by maintaining low temperatures as it is setting to a hardened ceramic (maintains less than 42° C. when setting), is readily formable and/or injectable, and yet can harden to high strength upon further reaction.

The ceramic composite material is bioresorbable and its mechanical properties may be adjusted by manipulating composition ratios, or physical characteristics of the component particles, so as to provide desired characteristics to meet the demands of the particular therapy and/or implant site. The composite material preferably includes at least one additive material. The additive material may serve to alter the flow and cure characteristics of the composite material prior to setting to a hardened state. The additive material may beneficially improve the handling properties of the composite material, and in an embodiment may prevent the hydrated formulation having a consistency of an excessively thin, liquid for injection and the resultant undesired migration of the thin liquid material away from the surgical site after delivery, and prior to setting.

In an embodiment, the composite material may be prepared into preformed shapes suitable for implant, for example, by having been cast into shaped articles for implant, for example, by being formed into objects such as bone plates, bone screws and other fixtures and medical devices, including veterinarian applications, which are bioresorbable and/or ossifying.

In another embodiment, the composite material may be provided as a dry combination, and upon hydration with an added hydrating fluid, presents a flowable mixture which is capable of being injected through a needle or cannula to a treatment site in a living being, whereupon curing may be completed.

In still another embodiment, the composite material may be provided as dry combination suitable for mixing with a hydrating fluid, and may be provided as a component of a kit, also including other components that may be employed for the practice of the material in a bone repair application, such as instructions for use, accessories for mixing with a hydrating fluid or delivering and placing the hydrated cement (such as cannulas, mixing devices, delivery devices, syringes, mixing spatulas, mixing containers, one-way, selectively permeable, pressure relief valve). The kit optionally may contain a hydrating fluid, or accessories which may be used for preparing a suitable hydrating fluid (e.g., syringe, cell enrichment centrifuge, sterile filters).

These and other features of the invention are accomplished by the composite material of the invention including a bioresorbable, apatite-forming composition in intimate contact with a biocompatible additive material in an amount effective to impart a selected characteristic to the composite.

The composite material of the invention may be obtained by providing one of more reactants, selected from a group of a powdered calcium compounds in the form of selectively sized powder particles, said powder particles having a size in the range of about 1 pm to 50 um and selected from the group consisting of monocalcium phosphate monohydrate, monocalcium phosphate anhydrous, monocalcium phosphate monohydrate, dicalcium phosphate anhydrous, dicalcium phosphate dehydrate, octacalcium phosphate, alpha-tricalcium phosphate, beta-tricalcium phosphate, amorphous calcium phosphate, calcium deficient hydroxyapatite, non-stoichiometric hydroxyapatite, tetracalcium phosphate, $CaSO_4$, $CaSO_4.0.5H_2O$, $CaSO_4.2H_2O$, $CaO$, $Ca(OH)_2$, $CaCO_3$, optionally buffering agents, such as sodium phosphate dibasic dihydrate salt, and mixtures thereof in the presence of a limited quantity of fluid, such as water, saline, buffered saline, to produce a hydrated precursor in the form of a composition that is injectable and flowable. The composite materials contemplated herein are capable of promoting the conversion of the reactants to an apatitic calcium phosphate as the cement reaction proceeds. The conversion is associated with hardening of the composite material, and produces an apatitic calcium phosphate. The composite material may further contain an additive material in an amount effective to impart a selected characteristic to the composite.

Definitions

"Apatitic"—"Apatitic" is used to describe a Calcium Phosphate material with the crystal structure of, or similar to, apatite.

"Biocompatible"—The term "biocompatible", as used herein, means that the material does not elicit a substantial detrimental response in the host.

"Bioresorbable"—"Bioresorbable" refers to the ability of a material to be resorbed in vivo. "Full" resorption means that no significant extracellular fragments remain. The resorption process involves elimination of the original implant materials through the action of body fluids, enzymes or cells. Resorbed calcium phosphate may, for example, be redeposited as bone mineral, or by being otherwise reutilized within the body, or excreted.

"Effective Amount"—An effective amount of a supplemental material is an amount sufficient to impart the desired mechanical or chemical property to the composite.

"Hardening"—"Hardening" refers to the process by which the hydrated precursor is transformed into a hardened apatitic material. The apatitic material is considered to be "hardened" when it is a substantially non-formable solid. Such a hardened apatitic material has minimal compressibility and tends to undergo plastic as opposed to elastic deformation.

"Hydrated precursor"—The term "hydrated precursor", as used herein, refers to the paste or putty formed by hydration of the dry reactants in the presence of a limited amount of aqueous solution (i.e., less than approximately 1 mL aqueous solution/0.5-5 g precursor powder). The hydrated precursor may comprise both reactants and products, in various combinations, depending on the extent to which the conversion has progressed. Both the "injectable" and "formable" precursor pastes described herein are hydrated precursors. Preferred "injectable" hydrated precursors have a consistency appropriate for delivery through a needle of gauge 6 (having a nominal inner diameter of 0.173 inches) or narrower.

"Injectable"—The term "injectable" as used herein refers to any material that is suitable for delivery by syringe and passing through a needle or cannula. A material will be readily injectable for the purposes described herein if the material can be injected using a traditional syringe, and eject at least 90% of the mass in the syringe, using a comfortable hand pressure of no greater than 22.5 poundfeet, through an 8.5 gauge (having a nominal inner diameter of 0.136 inches) cannula.

"Reactive"—"Reactive" is used herein to refer to the ability of a fine Calcium Phosphate powder, when mixed with liquid, to form a hydrated precursor to undergo conversion to the apatitic material of the present invention via cementitious hardening of the precursor materials.

"Swelling Additive"—A "swelling additive" is defined as a discrete hydrogel particle, that may be additionally provided in a cementitious material, and, upon initial exposure to a hydrating fluid to form a hydrated precursor, the swelling additive will absorb the hydrating fluid, and retain the fluid within the molecules of the particle material, such that the fluid cannot be expelled from the additive material, even under compression. The swelling additive remains a discrete particle that is a hydrogel, where the particles are suspended within the balance of the composition, and has a minimal impact upon the overall viscosity of the composition. Such a swelling additive may further be elastically deformable. Additionally, such a swelling additive particle may be capable of, at least temporarily, sequestering at least a portion of the hydrating fluid within its volume, so that portion of the hydrating fluid is not readily available as the apatitic calcium phosphate reaction, at least initially, proceeds. Where the swelling additive is a material that resorbs more quickly than the apatitic material of the cement, the swelling additive would serve as a porogen as the cement would set while encompassing the swelling additive, which would leave a pore of its general hydrated shape as the material is processed or resorbed.

BRIEF DESCRIPTION OF THE FIGURES

FIG. 2—Handleability assessment scale.

DETAILED DESCRIPTION OF THE INVENTION

Figure 1:
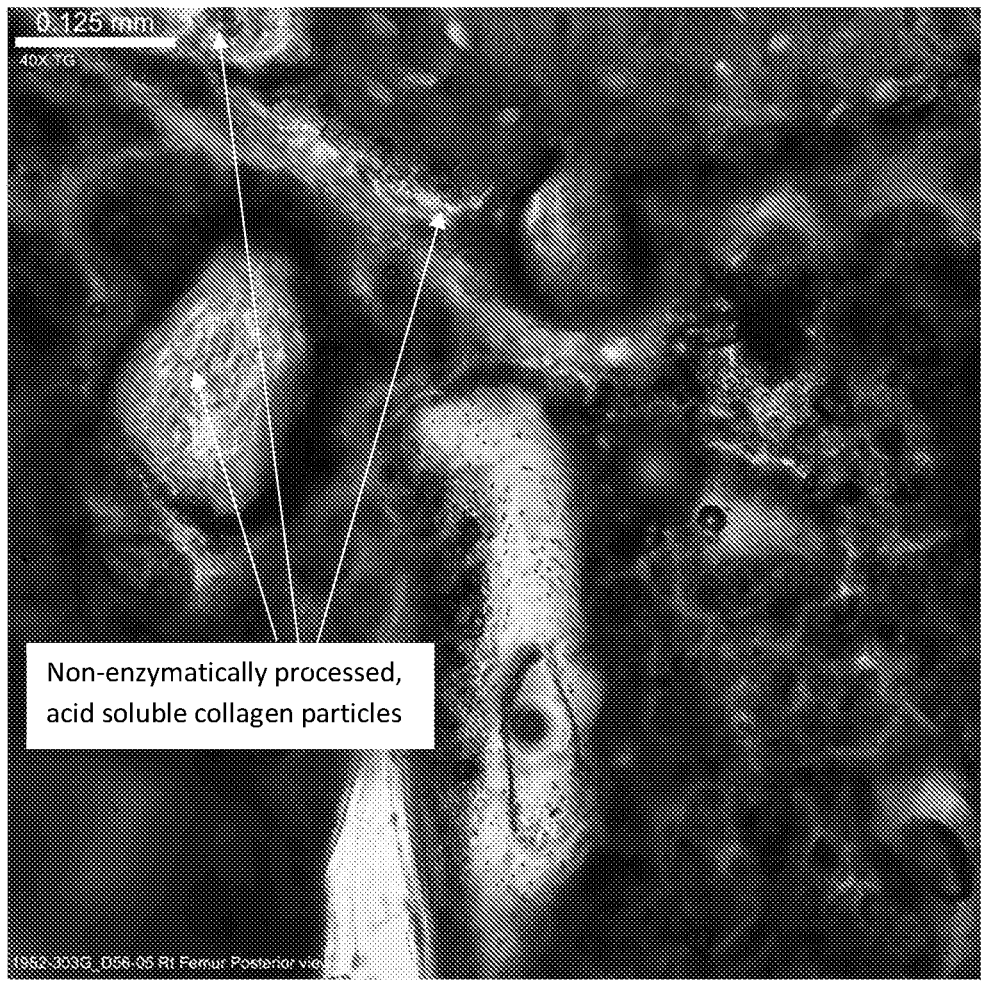
FIG. 1—An image of a trichome stained cross-section of the implanted material.

The present invention is directed to a composite material adapted for use in the repair and growth promotion of bone tissue, as a bone substitute composite. The composition comprises a biocompatible and bioresorbable, apatite forming calcium phosphate cement composition combined with at least one suitable biocompatible matrix or additive.

In one aspect, the invention provides for a composite material comprising a bioresorbable, apatite forming calcium phosphate material and additional bioresorbable additive materials which can be prepared under mild conditions at room or body temperature (e.g., 20-40° C.). The composite material may be applied to bone-contacting surfaces of prosthetic devices, for use as a bone cement. It may be used as a synthetic bone graft medium, where it may be applied directly to bone defects as a filler, where it is capable of promoting the growth of new bone tissue. Alternatively, the composite material may be used to fabricate fixtures or devices, such as screws, spacers, and plates, which under appropriate circumstances will be resorbed and replaced by bone. The composite may also be used free standing in non-osseous tissue. When a pharmaceutically active component is added to the composite, it serves as a drug delivery device. Release of the pharmaceutically active component may occur over a long period of time after implantation as the composite slowly biodegrades.

Preparation of the Composite Material.

The composite material of the present invention may be prepared by combining an apatite forming calcium phosphate reactive composition with one or more selected additive materials. In an embodiment, the reacted apatitic calcium phosphate may serve as a matrix, forming a continuous phase, and the additive forms discrete particles as a discontinuous phase, distributed throughout the volume of the matrix, with the additive particle distribution being random or non-random. The apatite forming calcium phosphate precursor, in its initial paste form (i.e., as a hydrated precursor), typically maintains a pH of about 6-7, and is therefore compatible with a wide range of additives without deleterious effect. The additive material is selected based upon its compatibility with calcium phosphate, and its ability to impart sought-after properties (e.g., biological, chemical or mechanical) to the composite, whether in the form of the hydrated precursor cement, or through to the fully-set cement material, which properties would be desirable for a particular therapeutic purpose or clinical application. For example, the additive material may be selected to improve tensile strength and hardness, increase fracture toughness, alter elasticity, provide imaging capability, and/or alter flow properties and setting times of the reacted apatitic calcium phosphate, when compared to a similar mixture lacking the particular selected additive.

The additive material may be added to the composite in varying amounts and in a variety of physical forms, dependent upon the anticipated therapeutic use. By way of example only, the additive material may be in the form of sponges (porous structure), meshes, films, fibers, gels, filaments, spheres, rods, flakes, regular or irregular granules, or particles, including micro- and nanoparticles. The additive material itself may be a composite mixture. The additive material may be a particulate additive which is intimately mixed with the composite material that reacts to the resorbable apatitic calcium phosphate. The additive material may serve as a matrix for the apatite forming calcium phosphate reactants, or the reacted apatite calcium phosphate, which is embedded or dispersed within the matrix. Alternatively, the composite material of apatitic calcium phosphate reactants may serve as a matrix for the additive material, which is dispersed therein. In an embodiment, an additive material may be applied as a coating onto a reacted apatitic calcium phosphate body, for example, as a post-fabrication coating to retard resorption time or otherwise affect the material properties of the reacted apatite calcium phosphate. Additionally, the additive material may be coated with apatitic calcium phosphate.

The additive materials are desirably biocompatible, that is, there is no detrimental reaction induced by the material when introduced into the host. In many instances, it is desirable that the additive material also be bioresorbable.

Furthermore, additive materials could include allograft or xenograft bone materials. For example, the bone materials may be powdered bone, or granules, chips or fibers composed of cancellous, cortical bone, combinations thereof. The additive may be a demineralized bone matrix (DBM), which, when incorporated into the composition as an additive would promote osteoinduction and establishment of tissue integration into the implanted material. DBM may be produced by treating bone materials in a manner that removes the mineral content, such techniques are known to those skilled in the art. DBM may beneficially be incorporated in any of the various embodiments described herein. The additive may be an anorganic bone material (ABM), which when incorporated into the composition as an additive would promote osteoinduction and establishment of tissue integration into the implanted material. ABM may be produced by treating bone materials in a manner that removes the organic content, such techniques are known to those skilled in the art. ABM may beneficially be incorporated in any of the various embodiments described herein.

The implantable composite materials may be prepared as a hydrated precursor in the form of an injectable composition, or a paste, by addition of a fluid, such as water, saline, buffered solution, or a physiological fluid or isolated fraction thereof, to a mixture of an apatite forming calcium phosphate reactants and one or more additive materials. Alternatively, a mixture of the additive material with hydrated precursor powders can be prepared as a paste or putty. In cases where the additive material is to be dispersed within or reacted with an apatite forming calcium phosphate matrix, water may be added to one of the precursor calcium phosphates to form a hydrated precursor paste, the resulting paste may be mixed with an amount of additive material, and the second calcium phosphate source for the reactants is then added. Alternatively, the calcium phosphate sources which make up the apatite forming calcium phosphate precursor powder may be premixed, hydrating fluid may then be added and then the additive material is added.

In an embodiment, the apatite forming reactants are mixed outside of the body, yielding a formable composite material in the form of a hydrated precursor material having a physical integrity suitable for application to a surgical site. Conversion to the apatitic material generally is completed after application to the surgical site. In an embodiment, the conversion reaction to apatitic material is initiated by adding a hydrating fluid, for example water, or saline, to a mixture of the dry precursor components, thereby forming a hydrated precursor, which may be in the form of a flowable and injectable composition, or with less hydrating fluid added to the dry precursor components, a thicker composition, in the form of a paste or putty. Other aqueous agents, such as buffered saline, saline, blood, plasma, platelet rich plasma, platelet poor plasma, bone marrow aspirate, bone marrow aspirate concentrate, lipoaspirate, lipoaspirate concentrate, cell culture medium, serum or tissue culture medium may be used as the hydrating fluid. It is also contemplated that various buffering agents may be incorporated in a dry form (e.g., salt) into the other dry reagents, such that when a hydrating fluid is added, the buffering capacity is present in the hydrated composition. In an embodiment, sufficient water (or other suitable hydrating fluid) may be added to the precursor powders to form a flowable composition which is readily injectable with a narrow gauge needle, as may be used in orthopedic and dental applications. In various embodiments, the needle or cannula employed for injectable delivery of a bone cement composition has an inner diameter equal to or smaller than 6 gauge (having a 0.173 inch inner diameter), equal to or smaller than 8 gauge (having a 0.135 inch inner diameter), equal to or smaller than 10 gauge (having a 0.106 inch inner diameter), equal to or smaller than 12 gauge (having a 0.085 inch inner diameter), or equal to or smaller than 14 gauge (having a 0.063 inch inner diameter). The hydrated precursors of the composite materials should harden in a clinically relevant time period, typically less than 15 minutes, and preferably less than 10 minutes.

The resorbability of the implantable composite material of the invention is attributable in part to the porosity, crystallinity and chemical composition of its component materials. The composite material of the invention reacts to form a bioceramic in the form of an apatitic calcium phosphate, substantially similar to that found in natural bone. Porosity facilitates both the penetration of cells and cell processes into the bone substitute material matrix and the diffusion of substances to and from the matrix interior. Accordingly, low porosity composite materials resorb more slowly in vivo than those of high porosity. It is contemplated that the additive material incorporated into the reacted composite material may further serve as a porogen in the hardened composite, wherein the additive is resorbed more quickly than the surrounding apatitic calcium phosphate matrix, creating porosity in the void space that was previously occupied by the additive material.

Examples of additive materials that may serve as porogens include non-soluble materials, such as resorbable polymers, salts, and biopolymers. The pores created would correspond to the size of the additive material particles present at the time that the apatitic calcium phosphate matrix is hardened around the additive material particle. Ideally, the porogens would create pores that are of a size that encourages cellular infiltration and establishment of cellular populations that could lead to growth of the appropriate tissue type. Thus a non-soluble polymer is able to create heterogenous density areas, as the porogon precludes the cement setting in at least the area that is occupied by the particle. By way of contrast, a soluble polymer, when admixed into the hydrated precursor material would result in an overall reduction in density of the material as the soluble polymer would be carried in solution throughout the entirety of the hydrated matrix, thereby serving to create a homogenous reduced density in the material.

In preferred embodiments, in order to optimize ossification, the devices and objects formed from the reacted composite material may be seeded with bone-forming cells. This is most easily accomplished by placing the device in contact with a source of the patient's own bone forming cells. Such cells may be found in bone-associated tissue, blood or fluids, including concentrated cellular fractions processed from collected blood, bone-associated tissue, or fluids, exogenous fluids which have been in contact with bone or bone materials or regions, including the periosteum, cancellous bone or marrow.

In the practice of the various embodiments, it may be useful to surgically prepare a seating within the bone, by removing a portion of cortical bone at the desired implant site. Other steps may also be taken to augment ossification, including introduction as an additive material of bone forming cells harvested from the patient into the hydrated precursor of the composite device, or onto the reacted composite device; or incorporation of trophic factors or bone growth inducing proteins into the hydrated precursor of the composite device, or onto the reacted composite device. Use of non-autologous bone cells is also within the scope of the invention if the desired amount of bone regeneration occurs prior to host rejection of the bone forming cells. Thus, cells or tissues obtained from primary sources, cell lines or cell banks may all be useful in certain embodiments.

In other embodiments, a composite material is provided comprising apatite forming reactants and a non-resorbable or poorly resorbable material. Suitable non-erodible or poorly erodible materials include dextrans, polyethylene, polymethylmethacrylate (PMMA), carbon fibers, polyvinyl alcohol (PVA), poly(ethylene terephthalate)polyamide, bioactive glasses, and those compounds listed previously for use in bone glues or putties.

Another use is to permanently imbed useful objects, such as a pin or reinforcing mesh, into bone itself. The object serves as an anchor for the stable attachment to natural bone. This is particularly useful in the attachment of ligaments and tendons to bone. Objects comprising bioresorbable and ossifying apatitic calcium phosphate and a suitable non-resorbable hardware may be placed into a bone and further secured with additional apatitic calcium phosphate material or composite material in a bone glue formulation. The hardware then becomes embedded into the bone following reossification of the apatitic calcium phosphate.

In yet another embodiment of the invention, a composition is prepared by intimately mixing the apatite forming reactants with an additive which alters the resorption properties, setting time and/or flow characteristics of the composite. For example, in one embodiment, lubricating polymers or liquids may be added to the composite to improve the flow characteristics of the composite for delivery to the host by syringe. The lubricant is preferably biocompatible and capable of rapid leaching from the bone substitute material composite following solidification of the apatitic calcium phosphate in vivo. Such suitable lubricants include, by way of example only, polymer waxes, lipids, silicone oils, and fatty acids. Lubricants may be used in a concentration of about 0.1 to about 30 wt %.

In yet another embodiment of the invention, a composition is prepared by intimately mixing the apatite forming reactants with an additive which alters the resorption properties, setting time and/or flow characteristics of the composite. In an embodiment, the additive is hygroscopic particles, such that the particle substance is capable of attracting and holding water molecules from the surrounding environment. This is achieved through either absorption or adsorption, with the absorbing or adsorbing substance becoming physically changed somewhat, such as through, for example, an increase in volume, boiling point, viscosity or other physical characteristic and properties of the substance, as water molecules can become suspended between the substance's molecules in the process. In an embodiment, the additive material is a hydrogel, where upon initial exposure to a hydrating fluid, the additive will be in the form of discrete particles that absorb the hydrating fluid, and retain the fluid within the molecules of the particle material, such that the fluid cannot be expelled from the additive material, even under compression. In this manner, the hydrogel particle would take in hydrating fluid, causing swelling of the particle, and when compression is applied, such as in the course of the material being forced through a constriction when injected, or kneaded manually, the particle would retain the fluid, and not release the fluid from within the particle when compressed. Such a hydrogel as an additive is termed a "swelling additive". This is not to be confused with an additive that would form a hydrogel throughout the entire volume of the composition, and necessarily would impact the viscosity of the entire composition. The swelling additive remains a discrete particle, that is a hydrogel, where the particles are suspended within the balance of the composition, and has a minimal impact upon the overall viscosity of the composition. Such a swelling additive may further be elastically deformable. Additionally, such a swelling additive particle may be capable of, at least temporarily, sequestering at least a portion of the hydrating fluid within its volume, so that portion of the hydrating fluid is not readily available to react with the apatite forming reactants. Such a swelling additive, as a hydrogel material within an cementitious reaction material would form a discrete particle contained within the volume of the cement as it is reacting, thereby forming a pore corresponding to the particular size and shape of the swelling additive particle after it is resorbed.

Upon implantation of the composition of apatitic forming calcium phosphate reactants bearing the swelling additive particles, when biological fluids and synthetic irrigation fluids will be present in excess, the cement reaction may proceed to completion by conversion of the reactants of the hydrated precursor to apatitic calcium phosphate. The swelling additive in this embodiment may be insoluble in the hydrating fluid, and upon exposure to the hydrating fluid, a suspension of the additive particles in the hydrating fluid may be created. By way of contrast, additive materials that are soluble in the hydrating fluid would result in a single-phase solution as the soluble additive material becomes solubilized in the hydrating fluid, such that there would remain no discrete particles, as would be found with a suspension of insoluble additive materials, as contemplated herein. Additive materials that are soluble in the hydrating fluid would be expected to increase the viscosity of the overall composition as their concentration is increased. Further, a suspension, as utilized for the various embodiments herein, is distinguishable from a colloidal suspension, which has been previously employed as gelling agent, or a gel, as a colloidal suspension would have particles homogenously suspended in the fluid, forming a three-dimensional structure caused by particle to particle interactions, as well as particle to hydrating fluid interactions. The insoluble swelling additive material, as contemplated herein, as it absorbs the hydrating fluid, may further provide lubricity to the hydrated precursor, and improve the flow characteristics of the composite for delivery by syringe, without increasing the viscosity of the overall composite mixture. Adding lubricity to the composite material is beneficial in allowing the hydrated precursor to be more easily ejected through a narrow opening, such as a syringe or cannula. Further, by virtue of the insoluble additive material, when hydrated, not increasing the viscosity of the mixture, the reaction rate is not detrimentally affected, as applicant's have noted that an increase in the overall viscosity of the hydrated precursor material is believed to impede the transfer of ions through the solution, resulting in an increased setting time of the composition.

In a particular aspect of the invention, the composition is prepared by intimately mixing the apatite forming calcium phosphate reactants with a swelling additive comprising particles of non-enzymatically-produced, acid-soluble collagen, which is commercially available as Kensey Nash Part No. 20003. Such non-enzymatically-produced, acid-soluble collagen may be added to the composite at up to 10% by weight of the apatite forming calcium phosphate reactants, so as to ensure a hard-setting composition suitable for use as a bone cement, for example, in orthopedic and dental applications. A hard-setting composition is defined as a material that has the same compressive strength as cancellous bone after 24 hours curing in a synthetic analog of biological fluid, such as phosphate buffered saline, at approximately (37° C.) body temperature. In other embodiments, the non-enzymatically prepared, acid-soluble collagen is added in a range that is less than 8% by weight of the apatite forming calcium phosphate reactants, less than 5 by weight of the apatite forming calcium phosphate reactants, less than 3% by weight of the apatite forming calcium phosphate reactants or less than 1.6% by weight of the apatite forming calcium phosphate reactants.

Acid-soluble collagen is characterized by being insoluble at normal physiological pH, but becomes more soluble at a pH of 4 or lower. Acid-soluble collagen that has been processed non-enzymatically is distinguishable from the more commonly produced enzymatically-processed form of soluble collagen, in that non-enzymatically-processed acid-soluble collagen will dissociate at a pH below 4, but not at physiological pH (i.e., pH 6-9), and when wetted at a physiological pH, the non-enzymatically processed acid-soluble collagen will imbibe fluid and swell as a hydrogel. Importantly, the non-enzymatically processed acid-soluble collagen, will absorb the hydrating fluid, and retain the fluid within the molecules of the particle material, such that the absorbed fluid cannot be expelled from the additive material, even under compression, and if compressed will react by deforming elastically without the release of the fluid that has been taken into the collagen particle. An advantage that is provided by the use of non-enzymatically processed acid-soluble collagen is that the ability to retain fluid even under compression, is beneficial for the use as an injectable material or implantable graft material, as when the hydrated precursor containing the non-enzymatically processed acid-soluble collagen, among other additives, if any, is exposed to compression, such as by kneading of the cement paste, or by being forced under compression through a constriction when being injected through a needle or cannula, the compression forces would not release the hydrating fluid from the swollen collagen particles. In this way, the benefit provided by the use of such swelling additive particles helps to prevent de-watering or phase separation of the cement when kneaded or injected. By way of contrast, it has been observed that an enzymatically-processed acid-soluble collagen, when wetted at physiological pH, will take in fluid, however, if exposed to compression, will readily release the fluid. Thus the enzymatically processed acid soluble collagen would not be as effective as preventing phase separation or dewatering when compressed as would occur when, for example, manipulated by kneading, or passed through a narrow opening by injection. Thus, the behavior of a non-enzymatically-processed acid-soluble collagen in a physiological solution retains a stronger affinity for fluid within the particle than does enzymatically processed acid-soluble collagen, and thus does not perform the same as would an enzymatically-processed acid-soluble collagen if used as an additive in an aqueous mixture. It is this characteristic that allows the non-enzymatically-processed acid-soluble collagen to function as a swelling additive as described above.

Non-enzymatically processed, acid-soluble collagen may be produced by milling a cleaned collagen source material, such as hides or skins. Typically the collagen materials are from any suitable animal source, for example, bovine, porcine, piscine, ovine, caprine, or other suitable sources. This tropocollagen resulting from non-enzymatic processing is unable to undergo spontaneous fibrillation under physiological conditions. The addition of a hydrating fluid, with a pH above 4, preferably, nearly neutral pH, will cause the non-enzymatically-produced, acid-soluble collagen to swell as it takes in the hydrating fluid, without solubilization. The swollen collagen remains as discrete particles, presents a discontinuous phase, carried within the apatitic calcium phosphate reacted composition, as a continuous phase. This can be seen in the image provided as FIG. 1, which is a magnified cross-section of a femur from a sheep having an 8 week implanted material described in example 4, the slide has been trichrome stained, where the discrete particles of non-enzymatically-produced, acid-soluble collagen are stained an orange hue, surrounded by the blue color of the hydroxyapatitic cement. In the image, the collagen particles have been highlighted, as can be seen, they remain as discrete particles within the reacted cement surrounding the collagen particles. It has been observed that as the collagen particles swell in the presence of the hydrating fluid, the particles may take on a lubricious nature, likely attributable to micro- and macro-ionic interactions between the swollen additive, the calcium salts, and the hydrating fluid. The lubricity provided by the inclusion of the non-enzymatically-produced, acid-soluble collagen, along with its ability to retain fluid, allows the apatite forming calcium phosphate reactant particles to more readily move relative to each other, and prevents clogging at an orifice when the composition is to be injected. Preferably, the lubricity of the cement composition can be further modified with additional additives materials. One such example is a low-molecular weight, hydrophilic polymer, such as polyethylene glycol, discussed below.

In addition to the non-enzymatically-processed acid-soluble collagen, described above, it is contemplated by the inventors that other natural polymers, e.g., polysaccharides, such as chitin and proteins, such as gelatin, or polynucleotides, may similarly function as swelling additives, that are capable of presenting as swollen discrete particles of hydrogel material, when admixed to the apatite forming calcium phosphate reactants composition, and swollen in the presence of a hydrating fluid. It is further contemplated that non-biodegradable swelling additives may beneficially be incorporated into the various embodiments of the inventions described herein. For example, hydrogel particles that are non-biodegradable may be made of similar polymers as are used in the manufacture of soft contact lenses, such as silicone hydrogels, or super absorbent polymers, such as polyacrylamide copolymer, ethylene maleic anhydride copolymer, and starch grafted copolymer of polyacrylonitrile. In circumstances where the composition is to be implanted, the synthetic polymer swelling additives are preferably biocompatible. The particles do not have a negative impact upon the setting time, but provide enhanced handling properties when mixed in with a hydrated precursor cement and a lubricant additive, by providing better injectability and cohesion, as evidenced by the lack of dissociation of the material when handled.

A composite material including one or more of the swelling additive materials described above, for example, the non-enzymatically-produced, acid-soluble collagen described above, or one of the hydrogel forming particles described above, will, upon hydration with a hydrating fluid, be of an initial volume, and as the particle swells in the presence of additional fluid, will increase in volume prior to setting to a final hardened form. This provides a benefit to the composite material in that the swelling of the composite material may occur as it is placed in the treatment site, causing there to be an outward pressure that aids in securing the composite material in place. Furthermore, the outward expansion of the composite material will result in better intimate contact between the hardened apatitic material and the surrounding tissue, such that surrounding tissue may more easily grow into the implant material to aid in osseointegration. As an added benefit, the swelling will only occur in the presence of excess fluid, thus ensuring that the full potential volume increase occurs after implantation.

In yet another particular aspect of the invention, the composition is prepared by mixing the apatite forming calcium phosphate reactants with at least two additive materials, wherein the first additive comprises at least one swelling additive, as has been described previously, for example, particles of non-enzymatically-produced, acid-soluble collagen, and a second additive comprises an amount of polymer. In an embodiment, the polymer of the second additive is a water soluble polymer. This water soluble polymer, upon addition of the hydrating fluid, becomes readily solubilized, and provides lubricity to the hydrated composition. In an embodiment, the water soluble polymer is a polyalkylene oxide, such as polyethylene glycol (PEG). In another embodiment, the water soluble polymer is any soluble polymer that provided lubricity while in solution, examples of such polymers include polyvinylpyrrolidone (PVP), polyvinyl alcohol (PVA), and Hyaluronic Acid, as non-limiting list of examples. The water soluble polymer may be provided in any molecular weight form that is capable of being solubilized readily, when it encounters the added hydrating fluid, and thereby is able to provide a lubricious property throughout the volume of the composition when hydrated. Preferably, the water soluble polymer is PEG, and is provided in an average molecular weight range from 1,000 to 20,000 Daltons, as an average molecular weight, preferably having an average of approximately 4,000 Daltons. The PEG may be added as a dry powder, at a rate of 0.005 to 0.05 grams of PEG to 1.0 gram of calcium salts. It is contemplated that lower molecular weight PEG may be provided as a wax, or even liquid form, for incorporation into the cementitious mixture. In an embodiment, the PEG may be provided at a rate of approximately 0.025 grams of PEG to 1.0 gram of calcium salts. The water soluble polymer may be added in any form, into the apatite forming reactant powder directly, to which may also be added a swelling additive, for example, the non-enzymatically processed, acid soluble collagen described previously. Preferably, the water soluble polymer may be incorporated into the collagen as it is being processed to the tropocollagen level of architecture, and together the collagen and water soluble polymer may be added to the apatitic calcium phosphate.

In yet another embodiment of the invention, the composite contains an apatite forming composition and a radiographic additive material for imaging the implant in vivo. Suitable electron dense materials include materials known in the art, such as titanium and barium oxide, in clinically relevant concentrations.

In a preferred embodiment, a composite material according to any of the various embodiments described herein, may be prepared with a Young's Modulus similar to bone of a living being. In another preferred embodiment, the particulate reacted apatitic calcium phosphate is pressed into a desired shaped and the pressed body is impregnated with the one or more additive materials, described previously. In yet another preferred embodiment, hydrated precursor materials of the apatite forming calcium phosphate cement are mixed with the one or more additive materials and the conversion to the apatitic material is initiated.

The composite material according to any of the various embodiments described herein, may also be prepared with varying degrees of porosity. In one embodiment, the use of a dry mixture of controlled particle size reactants leads to a porous composite material. Other methods of promoting porosity, such as chemical or physical etching and leaching, and resorbable porogens may be employed. Resorbable porogens are those that resorb more quickly than the remaining ceramic material, leaving pores in the matrix of the ceramic material as the resorbable porogens are processed by the body. The created porosity allows for establishment of tissue generating cells to enter, and allow for nutrient entry and waste disposal in the composite material as the cellular ingrowth occurs.

The inventive composite may also be used as a drug delivery system by incorporation of a biologically active material into the composite. For example, it is contemplated that the various embodiments described herein may further be combined with one or more biologically active agents, such as an effective amount of growth factors, drugs, antibiotics, cells.

In another embodiment, the composite material may be provided as a kit useful by the operator for performing a surgical procedure. The kit may comprise any of the cement compositions and optionally a hydrating fluid, as described herein, and further provided with one of more of: instructions for use, accessories for preparing the cement mix, accessories for delivering the cement mix to the desired site. The accessories for preparing and delivering the cement mix may include a syringe, a syringe check-valve, to selectively allow the passage of air in one direction, but prevent the passage of fluid through the valve, at least one cannula or needle capable of being affixed to a syringe body, a mixing system syringe, and optionally a spindle drive for additional mechanical leverage when delivering the composition. Where the hydrating fluid is to be a cell enriched fluid, the kit may include the cement components and device for preparing the cell enriched fluid, such as a processing unit to prepare a fraction from whole blood, such as platelet rich plasma, or the hydrating fluid may be bone marrow aspirate or an enriched fraction thereof, or lipoaspirate or an enriched fraction thereof. A device for preparing enriched fractions from a biological fluid is described in US Patent Application No. 2013-0244856.

Without being limited to a particular theory, for a composition including the apatite forming cement components and at least one swelling additive material, for example, one or more of a non-enzymatically processed, acid-soluble collagen, gelatin, or chitin, it is thought that upon incorporation of a hydration fluid, the conversion from calcium phosphate powders to a hardened apatitic calcium phosphate would begin, but the conversion rate is such that there would be at least a minimum working time (before there is substantial hardening) that allows the swelling additive particle to imbibe a portion of the fluid, causing the particles to swell, and at the same time, starving the conversion reaction of fluid. The swollen additives serve to provide a lubricious property, which may further be enhanced by the inclusion by an amount of a water soluble polymer lubricant, such as a polyalkylene oxide, preferably polyethylene glycol. In an embodiment, the amount of water soluble polymer added is of a concentration that provides lubricity or enhanced injectability, without substantially affecting the overall viscosity of the hydrated composition. Applicants have found that addition of 4000 Dalton PEG, added as a powder at a rate of 0.025 grams of PEG to 1.0 gram of calcium salts provides additional lubricity to the composition when hydrated, but no detrimental effect to reaction rate. The hydrated composition is suitable for injection through a narrow gauge needle, facilitated by the presence of the swelling additive and the polymer. In contrast, the same concentration of apatite forming reactant components, lacking a swelling additive, when hydrated similarly, would immediately be too runny to remain at the site of injection, as it would migrate easily. Previously, viscosity modifiers that are soluble in the hydrating fluid would have been incorporated (such as carboxymethylcellulose (CMC)); however, this method of increasing viscosity of the overall composition would be expected to slow down the cement reaction, and additionally serves to homogenously reduce the density of the hardened composition, rather than heterogeneously reducing density by the creation of pores, as would occur due to the incorporation of swelling additives described herein. Thus, the surprising benefit of a swelling additive provides the benefit fluid control uptake, of easily being injected, and being of a viscosity that tends to remain at the site of injection. Continued exposure to fluids, at the site of injection, will result in a volumetric increase of the cement composition, as the swelling additive continues to draw in excess fluid.

In practice of the various embodiments described herein, the process of providing a readily injectable bone cement composition comprises: (a) providing an apatite forming calcium phosphate reactant material, at least one swelling additive, and optionally, a second additive in the form of a water soluble polyalkylene oxide, (b) adding an amount of hydrating fluid to the dry components in an amount that when mixed, will immediately form a hydrated precursor that is of a desirable viscosity for injection, without detrimentally increasing the setting time or negatively affecting the rate of cement reaction of the composition; (c) delivering the hydrated precursor by injection to a desired site; and (d) allowing the curing of the composition to a hardened material having a hardness similar to, or exceeding that of bone tissue. In step (b), while the composition is exposed to the hydrating fluid, the at least one swelling additives absorb and swell with the fluid to form hydrogel particles that are capable of imparting lubricity to the composition to aid in injection. Once the composition is injected, in step (c) to the treatment site, the inventive compositions remains in place without migrating, whereupon continued exposure to fluids, such as body fluids universally present at the treatment site, enable the entire composition to swell within the treatment site, enhancing the integration of the cement material into the treatment site. Once the cement material is fully hardened, the body will process the readily resorbable components, such as the swelling additives, or other additives, leaving porosity throughout the entirety of the implanted material, into which cellular infiltration and waste and nutrient flow may occur, aiding in tissue integration into the implant.

Testing Methodology and Physical Characterization of Compositions.

Injectability Test Protocol

The injectability of a hydrated cement precursor was determined quantitatively by preparing approximately 6 mL of the cement slurry, by combining the dry and liquid components, having the desired component ratios, in the barrel of a 14 mL Medmix P-system mixing syringe, and mixing vigorously for 30-45 seconds. An 8.5 Ga, 4" cannula was attached to the distal end of the mixing syringe via luer lock connection. An injection sleeve, provided as part of the Medmix P-system, was added to convert the Medmix P-system mixing syringe from a mixing mode to an injection mode as a syringe device. Within 3 minutes from the initial combining of hydrating fluid to the dry components, the loaded syringe with the mixed cement slurry was loaded into a fixture capable of securing the syringe body in place and advancing the plunger as necessary for operation in the testing device. The fixture and syringe were attached to an Instron Single Column Test Stand having a 1 kiloNewton load cell. The plunger position was noted on the syringe barrel, and the testing was performed by the Instron Test stand depressing the plunger at a rate of 2 inches/minute, until a maximum force of 22.5 pound feet was achieved. The operator will assess whether liquid was dispensed from the syringe, indicative of the effect of phase separation, similar to filter pressing, where solids are retained in the syringe barrel, but the liquid was driven out during the injection operation, indicating that the sample was not properly injectable. A cement mix that is properly injectable would readily flow out of the syringe as a homogeneous material, and not phase separate substantially as injection force is applied.

After the Instron device has advanced the plunger to the specified maximum force, the plunger location is again noted on the syringe barrel. By comparing the initial plunger location to the second plunger location, the injected volume will be calculated and recorded to determine the percent of the material that is injected over the course of the test.

A composition is deemed to be adequately injectable when the average percent of the material that can be injected from the syringe is greater than 90%, with an injection force that does not exceed 22.5 pound feet, per the Instron Single Column Test Stand.

Cement Setting Time Protocol

The setting time of a hydrated cement precursor mixture was determined quantitatively by mixing the powder, dry components with an appropriate amount of hydrating fluid, as set forth in the examples, and recording the time. The powder and fluid were mixed thoroughly to distribute the hydrating fluid throughout the volume of cement powder to form a hydrated precursor cement. The hydrated precursor cement was then transferred into VICAT molds having an inner depth of 4 mm and an inner diameter of 7 mm. At a time point that is 3 minutes and 30 seconds after the fluid addition to form the hydrated precursor, the cement filled molds are placed into a solution of phosphate buffered saline at 37° C. to simulate a biologic environment. At a time point of 5 minutes, a mold is removed from the PBS solution, and blotted dry, then placed on a VICAT needle apparatus, and at a time point of 5 min and 15 seconds, the VICAT needle is released. At a time point of 5 min and 30 seconds, the penetration of the VICAT needle into the test block is recorded. The VICAT needle was wiped down and prepared for additional testing of samples. The testing of samples was repeated at 1 minute intervals.

A composition is deemed to have adequate setting time characteristics when the average time for the sample to set was less than 10 minutes. A cement was deemed to set adequately when the VICAT needle penetrated no more than 1 mm into the sample when tested.

Handleability Assessment Protocol

The handling qualities of a hydrated cement precursor mixture were assessed by mixing the powder, dry components with an appropriate amount of hydrating fluid, as set forth in the examples. The hydrated precursor cement was then manipulated by gloved hands, and rolled into a ball, approximately 1-2 cm in diameter. The operator would observe the cohesiveness of the hydrated precursor, or note tendencies to leave material on the glove hand while handled. An ideal cement useful for filling tissue voids, would provide a hydrated precursor, prior to setting, that is easily formed, self-adherent, and leaves little, or even, no trace of the material on gloves that have been handling the material. While a subjective assessment, the handling of the hydrated precursor was assessed a value of 0-5, where the lower number presents the more desirable properties, according to the following scale (FIG. 2).

0—handling of the hydrated precursor leaves no material on the glove, and a visible residue on less than 10% of the glove area that had contacted the hydrated precursor. Rolling a ball with the hydrated precursor does not result in visible reduction of sample due to material adhering to the gloves.

1—handling of the hydrated precursor leaves almost no material on the glove, and a visible residue on less than 10% of the glove area that had contacted the hydrated precursor. Rolling a ball with the hydrated precursor does not result in visible reduction of sample due to material adhering to the gloves.

2—handling of the hydrated precursor leaves little or no material on the glove, and a visible residue on less than 50% of the glove area that had contacted the hydrated precursor. Rolling a ball with the hydrated precursor does not result in visible reduction of sample due to material adhering to the gloves.

3—handling of the hydrated precursor leaves thin layer of material on portions of the glove, and a visible residue on greater than 50% of the glove area that had contacted the hydrated precursor. Rolling a ball with the hydrated precursor does not result in visible reduction of sample due to material adhering to the gloves.

4—handling of the hydrated precursor leaves medium to large masses of material on the glove, and a visible residue on greater than 60% of the glove area that had contacted the hydrated precursor. Rolling a ball with the hydrated precursor results in visible reduction of sample due to material adhering to the gloves.

5—handling of the hydrated precursor leaves large masses of material on the glove, and a visible residue on greater than 70% of the glove area that had contacted the hydrated precursor. Rolling a ball with the hydrated precursor results in significant reduction of sample due to material adhering to the gloves.

A composition is deemed to have adequate handling characteristics when the handling is assessed as a score of 3 or lower, as the scores that are greater than 3 demonstrate characteristics of the material being difficult to work, such as a lack of cohesiveness of the hydrated precursor, reflected by the tendency of the mixture to adhere to the glove, rather than to itself. Poor handling qualities of the hydrated precursor cement would tend to result in poor placement of the material, or difficulties to the user in providing the cement precursor to the desired site.

The invention is further exemplified with reference to the following examples, which are presented for the purpose of illustration only and are not to be considered as limiting of the invention.

Example 1

Implantable Bone Cement Compositions

Cementitious materials suitable as bone cements are well known to those skilled in the art. Any material capable of hardening to an apatitic calcium phosphate could be utilized as a base cement formulation, to which the additive materials of the present invention may be added. The mechanisms related to the hardening of a bone cement composition into an apatitic calcium phosphate are well described in U.S. Pat. Nos. 4,518,430, 5,571,493, and 6,929,692.

The specific bone cement compositions to be used for comparison are disclosed in Table 1. The components will be combined by blending in any method known to those familiar with the art, for example, by being placed in a shaker-mixer (e.g., a Turbula™ mixer) for 30 minutes. The preferred cement composition comprises tetracalcium phosphate (TTCP), hydroxyapatite (HA), monocalcium phosphate monohydrate (MCPM), alpha-TCP (α-TCP), sodium phosphate dibasic dihydrate (SPDH), and a hydrating fluid of water or saline at the component percentages by weight percentage described herein.

TABLE 1

| | Component Name | | | | | |
|---|---|---|---|---|---|---|
| | TTCP | HA | MCPM | α-TCP | SPDH | Powder-to-Water Ratio |
| | | | Chemical Formula | | | |
| | $Ca_4(PO_4)_2O$ | $Ca_{10}(PO_4)_6(OH)_2$ | $CA(H_2PO_4)_2 \cdot H_2O$ | $\alpha\text{-}Ca_3(PO_4)_2$ | $NaH_2PO_4 \cdot 2H_2O$ | grams/mL |
| Example 1A | 23.13% | 1.27% | 4.35% | 70.10% | 1.15% | 3 |
| Example 1B | 23.13% | 2.27% | 4.35% | 69.10% | 1.15% | 3 |
| Example 1C | 13.00% | 2.27% | 4.35% | 79.23% | 1.15% | 3 |

The formulation described in representative Example 1B was prepared for testing per the setting time testing protocol, and was determined to have a setting time of 6 minutes, which is below the clinically desirable set time of 10 minutes; however, the formulation of Example 1B was observed to excessively adhere to a gloved hand and therefore had less than ideal handling characteristics. While the performance of example 1B is acceptable, when compared to existing cement formulations, it is desirable to provide a product with offers improved handling, injectability and setting time, relative to what is currently known.

The cement formulation of Example 1A and 1C were also tested as cement formulations that could be combined with the additive materials described herein. The cement of example 1A was determined to have an-average set time of 8.66 minutes. The cement of example 1C was determined to have an average set time of 5.66 minutes. It is contemplated that the addition of the additives materials described herein, could be added to any of these cement formulations described in example 1 A, B and C, to provide an acceptable cement composition.

Example 2

Implantable Compositions According to the Invention Containing a Swelling Additive The composition described in example 1B from Example 1 was combined with various additives, as disclosed in table 2. The additives could serve as a swelling additive example (non-enzymatically processed acid soluble collagen), while the remaining additives as comparative examples would not serve as a swelling additive (fibrous collagen, dietary, enzymatically processed, acid-soluble collagen, sodium alginate, carboxymethylcellulose (non-crosslinked)). The incorporation of the swelling additive was performed by blending the dry mixture in a shaker-mixer for 30 minutes.

Figure 3:
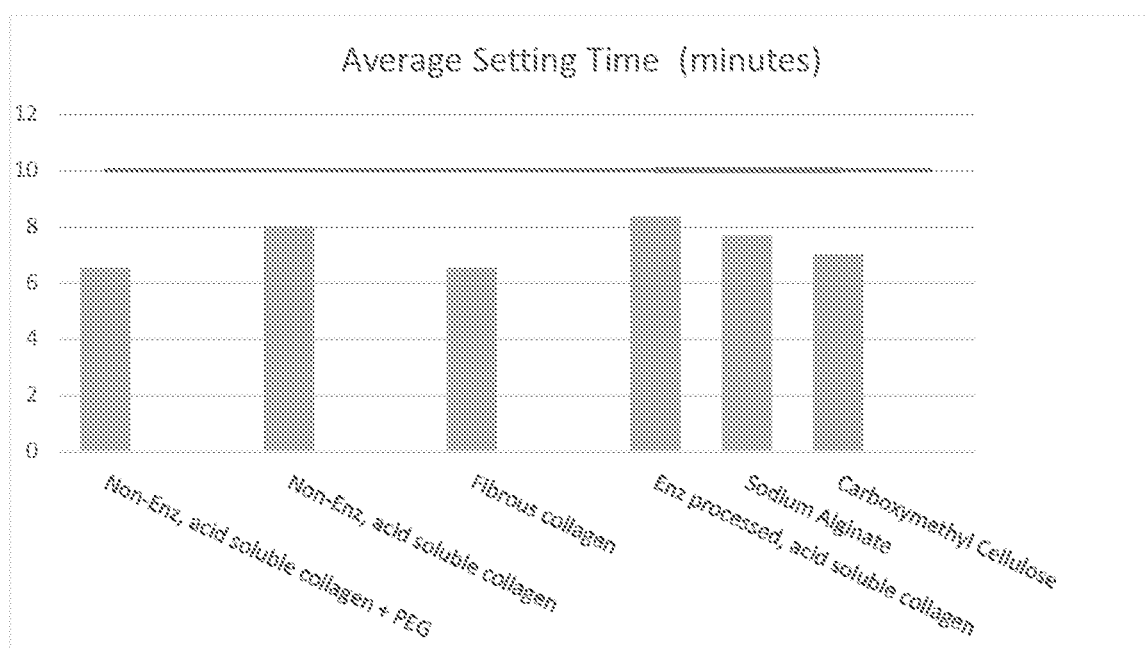
FIG. 3—Results from setting time assessment.
Figure 5:
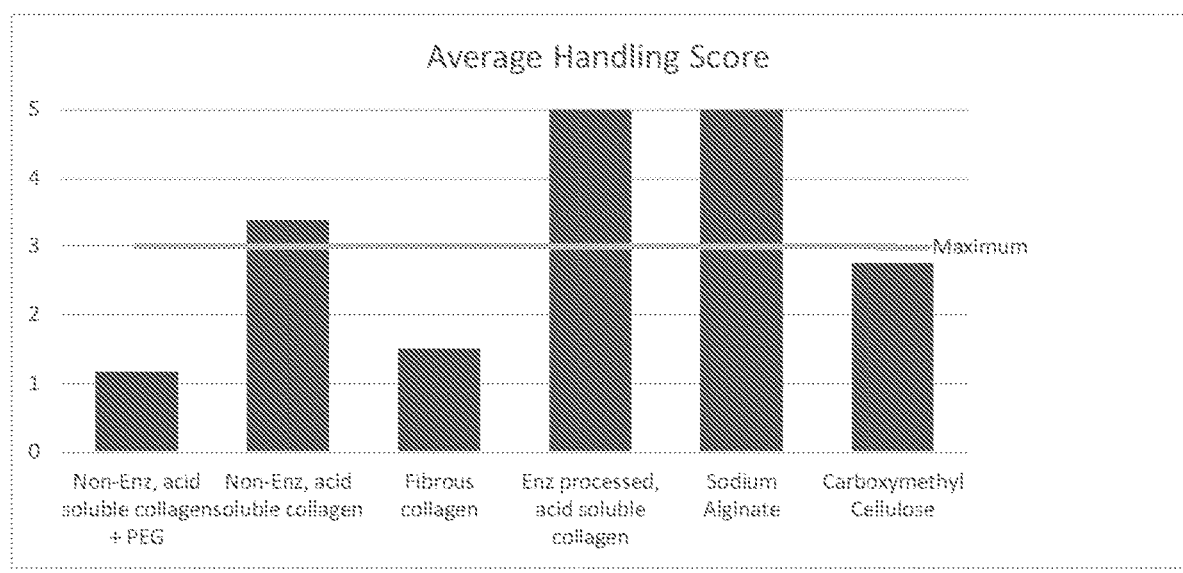
FIG. 5—results from handling assessment

The various compositions described in the examples were tested to assess the setting time, injectability and handling, with the data discussed below, and as presented in the attached figures, where the setting time assessment results are presented in FIG. 3, the injectability assessment results are presented in 4, and the handling assessment results are presented in FIG. 5.

11% on average of the cement was ejected from the syringe. The composition of comparative example 2B was assessed to have an average handling score of 1.5, per the scale provided in FIG. 2.

The composition of comparative example 2C comprising the cement mix with the dietary soluble collagen, an enzymatically-processed form of acid-soluble collagen, when tested had a 8.3 minute average setting time, and was able to be injected without having exceeded the threshold of 22.5 pound feet, such that 93% on average of the cement was ejected from the syringe. The composition of comparative example 2C presented poor handling properties and was assessed to have an average handling score of 5.0, per the scale provided in FIG. 2.

The composition of comparative example 2D comprising the cement mix with sodium alginate, when tested had a 7.7 minute average setting time, however, it was not suitably injectable, as the injection force required exceeded the threshold of 22.5 pound feet for injection, such that only 6% on average of the cement was ejected from the syringe. The composition of comparative example 2D presented poor

TABLE 2

| | TTCP | HA | MCPM | α-TCP | Non-E Acid Soluble Collagen | SPDH | Powder-to-Water ratio |
|---|---|---|---|---|---|---|---|
| Chemical Formula | $Ca_4(PO_4)_2O$ | $Ca_{10}(PO_4)_6(OH)_2$ | $CA(H_2PO_4)_2 \cdot H_2O$ | $\alpha\text{-}Ca_3(PO_4)_2$ | | $NaH_2PO_4 \cdot 2H_2O$ | |
| Example 2A | 22.00% | 2.20% | 4.10% | 65.70% | 5% | 0.01 | 2.12 |

| | TTCP | HA | MCPM | α-TCP | Fibrous Collagen | Dietary Soluble Collagen | Sodium Alginate | Carboxymethal Cellulose | SPDH | Powder-to-Water ratio |
|---|---|---|---|---|---|---|---|---|---|---|
| Chemical Formula | $Ca_4(PO_4)_2O$ | $Ca_{10}(PO_4)_6(OH)_2$ | $CA(H_2PO_4)_2 \cdot H_2O$ | $\alpha\text{-}Ca_3(PO_4)_2$ | | | | | | |
| Comp. Example 2B | 22.00% | 2.20% | 4.10% | 65.70% | 5% | 0.00% | 0.00% | 0.00% | 1.00% | 2.12 |
| Comp. Example 2C | 22.00% | 2.20% | 4.10% | 65.70% | 0.00% | 5% | 0.00% | 0.00% | 1.00% | 2.12 |
| Comp. Example 2D | 22.00% | 2.20% | 4.10% | 65.70% | 0.00% | 0.00% | 5% | 0.00% | 1.00% | 2.12 |
| Comp. Example 2E | 22.00% | 2.20% | 4.10% | 65.70% | 0.00% | 0.00% | 0.00% | 5% | 1.00% | 2.12 |

The composition of example 2A comprising the cement mix with the non-enzymatically processed, acid soluble collagen, when tested had an 8 minute average setting time, however, it was not suitably injectable, as the injection force required exceeded the threshold of 22.5 pound feet for injection, such that only 11% on average of the cement was ejected from the syringe. The composition of example 2A was assessed to have an average handling score of 3.38, per the scale provided in FIG. 2.

The composition of comparative example 2B comprising the cement mix with the fibrous collagen, when tested had a 6.5 minute average setting time, however, it was not suitably injectable, as the injection force required exceeded the threshold of 22.5 pound feet, such that only handling properties and was assessed to have an average handling score of 5.0, per the scale provided in FIG. 2.

The composition of comparative example 2E comprising the cement mix with the carboxymethylcellulose, when tested had a 7 minute average setting time, however, it was not suitably injectable, as the injection force required exceeded the threshold of 22.5 pound feet for injection, such that only 5% on average of the cement was ejected from the syringe. The composition of comparative example 2E was assessed to have an average handling score of 2.75, per the scale provided in FIG. 2.

Example 3

Incorporation of Polyethylene Glycol into Non-Enzymatically-Produced Acid-Soluble Collagen An amount of PEG was incorporated into the composition of Example 2A, at the rates disclosed in table 3. The PEG was obtained from a commercial supplier (Merck) and had an average molecular weight ranging from 2-10 kiloDaltons. The PEG component was incorporated into the composition by dissolving the PEG in a slurry made from the non-enzymatically processed, acid soluble collagen, which was then freeze dried and milled with a centrifugal mill to reduce the freeze dried matrix to smaller particles that one skilled in the art will recognize as readily capable of homogeneously mixing with the calcium phosphate powder blend.

TABLE 3

| Component Name | PEG | Non-Enz, acid soluble collagen |
|---|---|---|
| Chemical Formula | $C_{2n}H_{4n+2}O_{n+1}$ | — |
| Example 3A | 25% | 75% |
| Example 3B | 50% | 50% |
| Example 3C | 75% | 25% |

Example 4

Implantable Compositions According to the Invention Containing a Non-Enzymatically-Produced Acid-Soluble Collagen, with Polyethylene Glycol Incorporated into the Collagen The components having the ratio of PEG to non-enzymatically processed, acid soluble collagen of Example 3B was incorporated into composition of Example 1B, as disclosed table 4. The incorporation will be performed by blending the dry components in a shaker-mixer for 5 minutes.

TABLE 4

| | TTCP | HA | MCPM | α-TCP | PEG | Non-Enz, acid soluble collagen | SPDH | Powder-to-Water Ratio |
|---|---|---|---|---|---|---|---|---|
| Chemical Formula | $Ca_4(PO_4)_2O$ | $Ca_{10}(PO_4)_6(OH)_2$ | $Ca(H_2PO_4)_2 \cdot H_2O$ | $\alpha\text{-}Ca_3(PO_4)_2$ | $C_{2n}H_{4n+2}O_{n+1}$ | | $NaH_2PO_4 \cdot 2H_2O$ | grams/mL |
| Example 4 | 22.0% | 2.2% | 4.1% | 65.7% | 2.5% | 2.5% | 1.09% | 2.3 |

Figure 4:
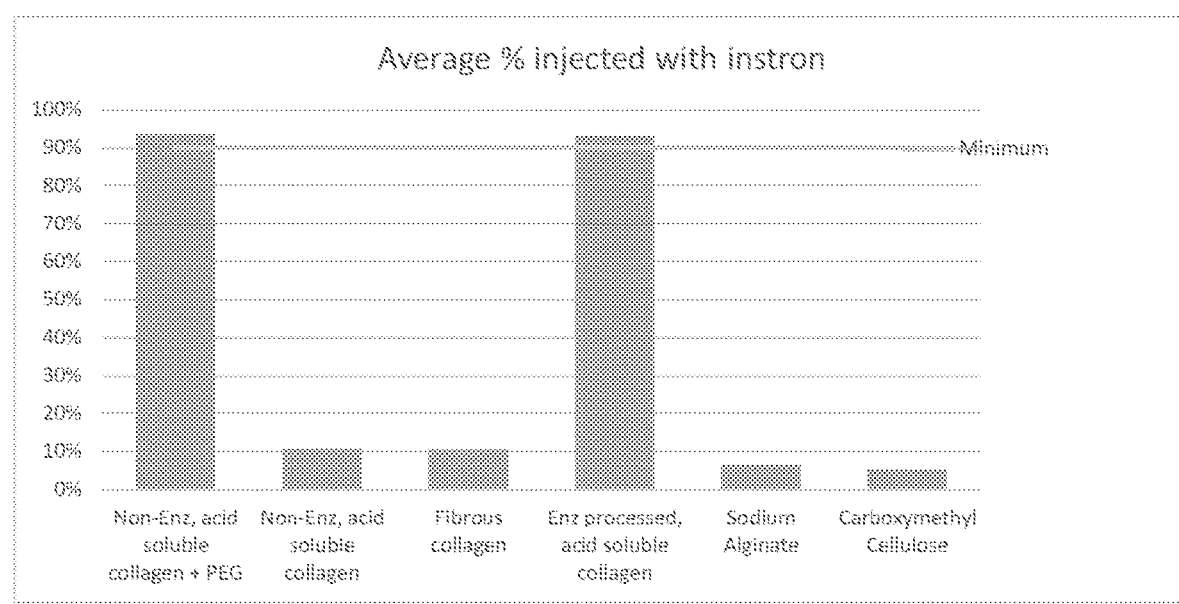
FIG. 4—Results from assessment.

The composition of example 4 comprising the cement mix with the non-enzymatically processed, acid soluble collagen and PEG when tested had a 6.5 minute average setting time, was able to be injected without exceeding the threshold of 22.5 pound feet for injection, where 94% on average of the cement was ejected from the syringe. The composition of example 4 was assessed to have an average handling score of 1.25, per the scale provided in FIG. 2. The example 4 results for the assessments of setting time, handling and injectability are presented in FIGS. 3, 4, and 5.

Example 4B

TABLE 4B

| | TTCP | HA | MCPM | α-TCP | PEG | Non-Enz, acid soluble collagen | SPDH | Powder-to-Water Ratio |
|---|---|---|---|---|---|---|---|---|
| Chemical Formula | $Ca_4(PO_4)_2O$ | $Ca_{10}(PO_4)_6(OH)_2$ | $Ca(H_2PO_4)_2 \cdot H_2O$ | $\alpha\text{-}Ca_3(PO_4)_2$ | $C_{2n}H_{4n+2}O_{n+1}$ | | $NaH_2PO_4 \cdot 2H_2O$ | grams/mL |
| Example 4B | 20.8% | 2.0% | 3.8% | 62.4% | 5.0% | 5.0% | 0.94% | 2.3 |

The composition of example 4B comprising the cement mix with the non-enzymatically processed, acid soluble collagen and PEG at twice the rate of example 4A, when tested had a 9 minute average setting time, was able to be injected without exceeding the threshold of 22.5 pound feet for injection, where 94% on average of the cement was ejected from the syringe. The composition of example 4 was assessed to have an average handling score of 1.25, per the scale provided in FIG. 2.

Example 5

Poly(Lactic-Co-Glycolic Acid) Co-Polymer Microspheres

Poly(lactic-co-glycolic acid) Co-Polymer Microspheres in the particle size distribution beneficial for use as porogens in a bioresorbable composite material are readily commercially available, from suppliers such as Sigma Aldrich. The particle size distribution (as determined by ASTM standard) is disclosed in a table 5.

TABLE 5

| PLGA Microsphere Particle Size Analysis Distribution Specifications | | |
|---|---|---|
| % of distribution between 150 and 300 microns - specification ≥90% | d99 < 365 μm | d10 > 150 μm |

Example 6

Implantable Compositions According to the Invention Containing a Non-Enzymatically-Produced Acid-Soluble Collagen, with Polyethylene Glycol Incorporated into the Collagen, and Poly(Lactic-Co-Glycolic Acid) Co-Polymer Microspheres To the composition of example 4, comprising the cement mix with the non-enzymatically processed, acid soluble collagen and PEG, was added an amount of PLGA microspheres from Example 5, at the component ratios disclosed in table 6. The microspheres were mixed with the dry powder ingredients by mixing in a shaker-mixer for 5 minutes.

The composition of example 6 comprising the cement mix with the non-enzymatically processed, acid soluble collagen, PEG and PLGA microspheres when tested was determined to have an 8 minute average setting time, was able to be injected without exceeding the threshold of 22.5 pound feet for injection, where 99% on average of the hydrated cement precursor was ejected from the syringe. The composition of example 6 was assessed to have desirable handling properties, and would have an average handling score of 3 or better, per the scale provided in FIG. 2.

Example 7

45S5 Bioactive Glass Powder in the particle size distribution beneficial for use as an osteostimulative additive in a bioresorbable composite material is readily commercially available. A supply of 45S5 bioactive glass powder was obtained from a commercial supplier (MO-SCI). The particle size distribution is detailed in table 7.

TABLE 7

| Bioactive Glass Particle Size Analysis Distribution Specifications |
|---|
| % of distribution between 106 and 212 microns - specification ≥80% |

Example 8

Implantable Compositions According to the Invention Containing a Non-Enzymatically-Produced Acid-Soluble Collagen, with Polyethylene Glycol Incorporated into the Collagen, and 45S5 Bioactive Glass Powder To the composition of example 4, comprising the cement mix with the non-enzymatically processed, acid soluble collagen and PEG, was added an amount of bioactive glass powder from Example 7, at the component ratios disclosed in table 8. The bioactive glass powder was mixed with the dry powder ingredients by mixing in a shaker-mixer for 5 minutes.

TABLE 6

| | Component Name | | | | |
|---|---|---|---|---|---|
| | TTCP | HA | MCPM | α-TCP | PEG |
| | | | Chemical Formula | | |
| | $Ca_4(PO_4)_2O$ | $Ca_{10}(PO_4)_6(OH)_2$ | $Ca(H_2PO_4)_2 \cdot H_2O$ | $\alpha\text{-}Ca_3(PO_4)_2$ | $C_{2n}H_{4n} + 2_{0n} + 1$ |
| Example 6 | 17.6% | 1.7% | 3.3% | 52.6% | 2.0% |

| | Component Name | | | |
|---|---|---|---|---|
| | Non-Enz, acid soluble collagen | SPDH | PLGA | Powder-to-Water Ratio |
| | | | Chemical Formula | |
| | | $NaH_2PO_4 \cdot 2H_2O$ | $[C_3H_4O_2]_x[C_2H_2O_2]_y$ | grams/mL |
| Example 6 | 2.0% | 0.9% | 19.8 % | 2.3 |

TABLE 8

| | Component Name | | | | |
|---|---|---|---|---|---|
| | TTCP | HA | MCPM | α-TCP | PEG |
| | | | Chemical Formula | | |
| | $Ca_4(PO_4)_2O$ | $Ca_{10}(PO_4)_6(OH)_2$ | $Ca(H_2PO_4)_2 \cdot H_2O$ | $\alpha\text{-}Ca_3(PO_4)_2$ | $C_{2n}H_{4n+20n+1}$ |
| Example 8 | 19.9% | 2.0% | 3.7% | 59.4% | 2.1% |

| | Component Name | | | |
|---|---|---|---|---|
| | Non-Enz, acid soluble collagen | SPDH | BA glass | Powder-to-Water Ratio |
| | | | Chemical Formula | |
| | | $NaH_2PO_4 \cdot 2H_2O$ | 5% $SiO_2$, 24.5% CaO, 24.5% $Na_2O$, 6% $P_2O_5$ | grams/mL |
| Example 8 | 2.1% | 1.0% | 9.9% | 2.3 |

The composition of example 8 comprising the cement mix with the non-enzymatically processed, acid soluble collagen, PEG and approximately 10% of the 45S5 Bioactive Glass Powder from example 7, when tested had a 7 minute average setting time, was able to be injected without exceeding the threshold of 22.5 pound feet for injection, where 99% on average of the hydrated cement precursor was ejected from the syringe. The composition of example 8 was assessed to have desirable handling properties, and was deemed superior to competitive products currently available on the market, and would be expected to have an average handling score of 3 or better, per the scale provided in FIG. 2.

Example 9

Demineralized Bone Matrix Powder

Human donor bone tissue can be granulated and demineralized into a powder as is known to those skilled in the art, for use as an orthopedic implant, and is available through various tissue banks. Samples were prepared incorporating Demineralized Cortical Bone powder obtained from a commercial tissue bank, having a particle size distribution between 212-850 microns. Additional testing was performed with smaller size particles to show that a distribution of particle sizes between 180-850 microns performed similarly.

Example 10

Implantable Compositions According to the Invention Containing a Non-Enzymatically-Produced Acid-Soluble Collagen, with Polyethylene Glycol Incorporated into the Collagen, and Demineralized Bone Matrix Powder To the composition of example 4, comprising the cement mix with the non-enzymatically processed, acid soluble collagen and PEG, was added an amount of demineralized bone matrix powder from Example 9, at the component ratios disclosed in table 9. The demineralized bone matrix powder was mixed with the dry powder ingredients by mixing in a shaker-mixer for 5 minutes.

TABLE 9

| | Component Name | | | | |
|---|---|---|---|---|---|
| | TTCP | HA | MCPM | α-TCP | PEG |
| | | | Chemical Formula | | |
| | $Ca_4(PO_4)_2O$ | $Ca_{10}(PO_4)_6(OH)_2$ | $Ca(H_2PO_4)_2 \cdot H_2O$ | $\alpha\text{-}Ca_3(PO_4)_2$ | $C_{2n}H_{4n+20n+1}$ |
| Example 10 | 16.5% | 1.6% | 3.1% | 49.4% | 1.7% |

| | Component Name | | | |
|---|---|---|---|---|
| | Non-Enz, acid soluble collagen | SPDH | DBM | Powder-to-Water Ratio |
| | | | Chemical Formula | |
| | | $NaH_2PO_4 \cdot 2H_2O$ | | grams/mL |
| Example 10 | 1.8% | 0.8% | 25.0% | 1.75 |

The composition of example 10 comprising the cement mix with the non-enzymatically processed, acid soluble collagen, PEG and the Demineralized Bone Matrix Powder from example 9, when tested had a 9 minute average setting time, was able to be injected without exceeding the threshold of 22.5 pound feet for injection, where 98% on average of the cement was ejected from the syringe. The composition of example 10 was assessed to have desirable handling properties, and was deemed superior to competitive products currently available on the market, and would be expected to have an average handling score of 3 or better, per the scale provided in FIG. 2.

Additional testing was performed with a sample of demineralized bone matrix powder having smaller size particles, at the same component ratios of Example 10, and revealed that similar performance could be obtained with a distribution of particle sizes of demineralized bone matrix particles between 180-850 microns.

By way of summary, and with reference to table 10, one can see that the desired qualities of a setting time below 10 minutes, an average handling score of 3 or better, and being injectable with less than 22.5 pound feet, as tested per the protocols described herein, are achieved with the tested cement formulation only with the embodiments that have a swelling additive, namely the non-enzymatically processed acid soluble collagen, and a lubricating soluble polymer, specifically PEG.

TABLE 10

| Test | Additive - meets set criteria y/n | | | | | |
|---|---|---|---|---|---|---|
| Injectability | y | n | n | y | n | n |
| Handieability | y | n | y | n | n | y |
| Setting Time | y | y | y | y | y | y |
| | Non-Enz, acid soluble collagen + PEG | Non-Enz, acid soluble collagen | Fibrous collagen | Enz processed, acid soluble collagen | Sodium Alginate | Carboxymethyl Cellulose |

It will be understood that the foregoing is merely descriptive of certain preferred embodiments of the invention and is not intended to be limiting thereof. The following claims cover all of the generic and specific features of the invention herein described in the text and accompanying drawings.

What is claimed is:

1. A composite material comprising:
   a. a reactive apatite forming composition comprising:
      i. discrete particles consisting of tetracalcium phosphate,
      ii. discrete particles consisting of hydroxyapatite,
      iii. discrete particles consisting of monocalcium phosphate monohydrate,
      iv. discrete particles consisting of alpha-tricalcium phosphate, and
      v. discrete particles consisting of sodium phosphate dibasic dihydrate,
   b. a water soluble polymer, and
   c. a swelling additive as a particle, wherein said swelling additive comprises non-enzymatically processed, acid soluble collagen, and
   wherein said composite material is in the form of a plurality of particles, and
   wherein upon being contacted with a hydrating fluid, said reactive apatite forming composition forms a hydrated precursor within which the swelling additive is suspended as a particle, wherein the hydrated precursor forms an apatitic calcium phosphate via cementitious hardening of the hydrated precursor.

2. The composite material of claim 1, wherein said composite material has a first volume at a first time of initial hydration, wherein the composite material has a second volume at a second, and later, time, that is greater than the first volume.

3. The composite material of claim 1, wherein said water soluble polymer comprises at least one of polyalkylene oxide, polyvinylpyrrolidone, polyvinyl alcohol, hyaluronic acid, or combinations thereof.

4. The composite material of claim 1, wherein said water soluble polymer comprises polyethylene glycol.

5. The composite material of claim 4, wherein said polyethylene glycol has an average molecular weight of 1,000 to 20,000 Daltons.

6. The composite material of claim 1, further comprising polymer microspheres.

7. The composite material of claim 1, wherein said composite material has an average setting time of less than 10 minutes and is injectable with less than 22.5 poundfeet of force through an 8.5 gauge cannula.

8. The composite material of claim 1, wherein said tetracalcium phosphate is present in an amount of from about 13 to about 23%, hydroxyapatite is present in an amount of from about 1.0 to about 2.2%, monocalcium phosphate monohydrate is present in an amount of from about 3.1 to about 4.35%, alpha-tricalcium phosphate is present in an amount of from about 49.4 to about 79.23%, and sodium phosphate dibasic dihydrate is present in an amount of from about 0.8 to about 1.15%, based on the total weight of the composite material.

9. The composite material according to claim 1, wherein the composite material comprises particles comprising both the water soluble polymer and the non-enzymatically processed, acid soluble collagen together.

10. The composite material according to claim 9, wherein the particles comprising both the water soluble polymer and the non-enzymatically processed, acid soluble collagen together are formed by dissolving the water soluble polymer in a slurry made from the non-enzymatically processed, acid soluble collagen, freeze drying the slurry, and then milling into particles.

11. The composite material according to claim 10, wherein the water soluble polymer comprises polyethylene glycol.

12. The composite material of claim 1, wherein the non-enzymatically processed, acid soluble collagen and the water soluble polymer are present in a combined amount of from 3.5 to 10 wt %.

13. The composite material according to claim 1, wherein the weight ratio of non-enzymatically processed, acid soluble collagen to water soluble polymer in the dry composite material is from 25:75 to 75:25.

14. The composite material according to claim 1, wherein upon being hydrated the composite material is injectable with less than 22.5 poundfeet of force through an 8.5 gauge cannula.

15. A composite material in the form of a plurality of particles and comprising a reactive apatite forming composition, a first additive, and a second additive, said reactive apatite forming composition comprising discrete particles consisting of tetracalcium phosphate, discrete particles consisting of hydroxyapatite, discrete particles consisting of monocalcium phosphate monohydrate, discrete particles consisting of alpha-tricalcium phosphate, and discrete particles consisting of sodium phosphate dibasic dihydrate, said first additive comprising a swelling additive comprising collagen, wherein said collagen comprises non-enzymatically processed, acid soluble collagen, and said second additive comprising a water soluble polymer comprising polyethylene glycol, and wherein upon being contacted with a hydrating fluid, said reactive apatite forming composition forms a hydrated precursor within which the swelling additive is suspended as a particle, wherein the hydrated precursor forms an apatitic calcium phosphate via cementitious hardening of the hydrated precursor.

16. The composite material of claim 15, wherein said composite material further comprises a third additive comprising poly(lactic-co-glycolic acid) co-polymer microspheres.

17. A kit comprising the composite material according to claim 15 and at least one of instructions for use, a mixing device, a delivery device, a hydrating fluid, a fluid processing unit, or a combination thereof.

18. A method of forming an apatitic composition, the method comprising the steps of: (a) providing a composite material in the form of a plurality of particles, the composite material comprising a reactive apatite forming composition, a first additive, and a second additive, said reactive apatite forming composition comprising discrete particles consisting of tetracalcium phosphate, discrete particles consisting of hydroxyapatite, discrete particles consisting of monocalcium phosphate monohydrate, discrete particles consisting of alpha-tricalcium phosphate, and discrete particles consisting of sodium phosphate dibasic dihydrate, said first additive comprising a swelling additive comprising collagen, wherein said collagen comprises non-enzymatically processed, acid soluble collagen, and said second additive comprising a water soluble polymer comprising polyethylene glycol; (b) adding an amount of hydrating fluid and mixing with said composite material to form a readily injectable hydrated precursor; wherein said first additive absorbs at least a portion of said hydrating fluid, and wherein the swelling additive is suspended within the hydrated precursor as a particle; (c) placing said composite material at a pre-determined site; and (d) allowing said composite material to harden to a solid.

19. The method of claim 18, wherein the swelling additive retains a portion of hydrating fluid and does not release said portion of hydrating fluid upon exposure to compressive forces experienced during step c.

* * * * *